United States Patent
Bartol et al.

(10) Patent No.: US 8,892,259 B2
(45) Date of Patent: *Nov. 18, 2014

(54) ROBOTIC SURGICAL SYSTEM WITH MECHANOMYOGRAPHY FEEDBACK

(71) Applicant: Innovative Surgical Solutions, LLC, Southfield, MI (US)

(72) Inventors: Stephen Bartol, Windsor (CA); Christopher Wybo, Royal Oak, MI (US)

(73) Assignee: Innovative Surgical Solutions, LLC., Wixom, MI (US)

( * ) Notice: Subject to any disclaimer, the term of this patent is extended or adjusted under 35 U.S.C. 154(b) by 311 days.

This patent is subject to a terminal disclaimer.

(21) Appl. No.: 13/627,283

(22) Filed: Sep. 26, 2012

(65) Prior Publication Data

US 2014/0088612 A1 Mar. 27, 2014

(51) Int. Cl.
*G05B 15/00* (2006.01)
*G05B 19/00* (2006.01)

(52) U.S. Cl.
USPC ........... 700/258; 700/245; 700/246; 700/247; 700/248; 700/251; 700/259; 700/260; 606/38; 600/554; 227/2

(58) Field of Classification Search
USPC ......... 700/245, 246, 247, 248, 251, 258, 259, 700/260; 606/38; 600/554; 227/2
See application file for complete search history.

(56) References Cited

U.S. PATENT DOCUMENTS

| | | |
|---|---|---|
| 3,200,814 A | 8/1965 | Taylor et al. |
| 3,565,080 A | 2/1971 | Ide et al. |
| 3,797,010 A | 3/1974 | Adler et al. |
| 4,817,628 A | 4/1989 | Zealear et al. |
| 5,284,153 A | 2/1994 | Raymond et al. |
| 5,284,154 A | 2/1994 | Raymond et al. |
| 5,775,331 A | 7/1998 | Raymond et al. |
| 6,324,432 B1 | 11/2001 | Rigaux et al. |

(Continued)

FOREIGN PATENT DOCUMENTS

| | | |
|---|---|---|
| EP | 1575010 A1 | 9/2005 |
| FR | 2920087 A1 | 2/2009 |
| WO | 0078209 A2 | 12/2000 |
| WO | 2007024147 A1 | 3/2007 |

OTHER PUBLICATIONS

Bartol, Stephen MD, and Laschuk, Maria MD, "Arthroscopic Microscopic Discectomy in Awake Patients: The Effectiveness of Local/Neurolept Anaesthetic", Canadian Spine Society Meeting, Vernon, BC, Canada, Mar. 2002.

(Continued)

*Primary Examiner* — Khoi Tran
*Assistant Examiner* — Adam Mott
(74) *Attorney, Agent, or Firm* — Quinn Law Group, PLLC

(57) ABSTRACT

A robotic surgical system for performing a surgical procedure within the body of a subject includes an elongate surgical instrument, a robotic controller configured to control the motion of the distal end portion of the surgical instrument, and a mechanomyography feedback system in communication with the robotic controller. The mechanomyography feedback system includes an elongate sphincter contraction sensor configured to monitor a physical response of a sphincter of the subject and to provide a mechanomyography signal corresponding to the monitored response. Additionally, the feedback system includes a processor configured to receive the mechanomyography signal, to determine if the received signal is indicative of an induced sphincter response, and to provide a control signal to the robotic controller if an induced sphincter response is detected.

20 Claims, 8 Drawing Sheets

(56) References Cited

U.S. PATENT DOCUMENTS

| | | | |
|---|---|---|---|
| 6,361,508 B1 | 3/2002 | Johnson et al. |
| 6,466,817 B1 | 10/2002 | Kaula et al. |
| 6,500,128 B2 | 12/2002 | Marino |
| 6,564,078 B1 | 5/2003 | Marino et al. |
| 6,760,616 B2 | 7/2004 | Hoey et al. |
| 6,807,438 B1 | 10/2004 | Brun Del Re et al. |
| 6,972,199 B2 | 12/2005 | Lebouitz et al. |
| 7,050,848 B2 | 5/2006 | Hoey et al. |
| 7,079,883 B2 | 7/2006 | Marino et al. |
| 7,177,677 B2 | 2/2007 | Kaula et al. |
| 7,207,949 B2 | 4/2007 | Miles et al. |
| 7,216,001 B2 | 5/2007 | Hacker et al. |
| 7,236,832 B2 | 6/2007 | Hemmerling et al. |
| 7,470,236 B1 | 12/2008 | Kelleher et al. |
| 7,522,953 B2 | 4/2009 | Kaula et al. |
| 7,578,819 B2 | 8/2009 | Bleich et al. |
| 7,582,058 B1 | 9/2009 | Miles et al. |
| 7,657,308 B2 | 2/2010 | Miles et al. |
| 7,664,544 B2 | 2/2010 | Miles et al. |
| 7,668,588 B2 | 2/2010 | Kovacs |
| 7,691,057 B2 | 4/2010 | Miles et al. |
| 7,892,173 B2 | 2/2011 | Miles et al. |
| 7,905,840 B2 | 3/2011 | Pimenta et al. |
| 7,942,826 B1 | 5/2011 | Scholl et al. |
| 7,959,577 B2 | 6/2011 | Schmitz et al. |
| 7,962,191 B2 | 6/2011 | Marino et al. |
| 7,981,058 B2 | 7/2011 | Akay |
| 7,991,463 B2 | 8/2011 | Kelleher et al. |
| 8,000,782 B2 | 8/2011 | Gharib et al. |
| 8,016,776 B2 | 9/2011 | Bourget et al. |
| 8,027,716 B2 | 9/2011 | Gharib et al. |
| 8,055,349 B2 | 11/2011 | Gharib et al. |
| 8,068,912 B2 | 11/2011 | Kaula et al. |
| 8,075,499 B2 | 12/2011 | Nathan et al. |
| 8,090,436 B2 | 1/2012 | Hoey et al. |
| 8,133,173 B2 | 3/2012 | Miles et al. |
| 8,137,284 B2 | 3/2012 | Miles et al. |
| 8,147,421 B2 | 4/2012 | Farquhar et al. |
| 8,165,653 B2 | 4/2012 | Marino et al. |
| 8,343,065 B2 | 1/2013 | Bartol et al. |
| 8,343,079 B2 | 1/2013 | Bartol et al. |
| 2001/0031916 A1 | 10/2001 | Bennett et al. |
| 2002/0038092 A1 | 3/2002 | Stanaland et al. |
| 2002/0165590 A1 | 11/2002 | Crowe et al. |
| 2003/0074037 A1 | 4/2003 | Moore et al. |
| 2004/0077969 A1 | 4/2004 | Onda et al. |
| 2004/0186535 A1 | 9/2004 | Knowlton |
| 2004/0230138 A1 | 11/2004 | Inoue et al. |
| 2004/0243018 A1 | 12/2004 | Organ et al. |
| 2005/0075578 A1 | 4/2005 | Gharib et al. |
| 2005/0085741 A1 | 4/2005 | Hoskonen et al. |
| 2005/0102007 A1 | 5/2005 | Ayal et al. |
| 2005/0240086 A1 | 10/2005 | Akay |
| 2005/0245839 A1 | 11/2005 | Stivoric et al. |
| 2005/0280531 A1 | 12/2005 | Fadem et al. |
| 2005/0283204 A1 | 12/2005 | Buhlmann et al. |
| 2006/0020177 A1 | 1/2006 | Seo et al. |
| 2006/0052726 A1 | 3/2006 | Weisz et al. |
| 2006/0135888 A1 | 6/2006 | Mimnagh-Kelleher et al. |
| 2006/0270949 A1 | 11/2006 | Mathie et al. |
| 2007/0038155 A1 | 2/2007 | Kelly, Jr. et al. |
| 2007/0265675 A1 | 11/2007 | Lund et al. |
| 2007/0276270 A1 | 11/2007 | Tran |
| 2008/0051643 A1 | 2/2008 | Park et al. |
| 2008/0058656 A1 | 3/2008 | Costello et al. |
| 2008/0167695 A1 | 7/2008 | Tehrani et al. |
| 2008/0234767 A1 | 9/2008 | Salmon et al. |
| 2008/0287761 A1 | 11/2008 | Hayter et al. |
| 2008/0306363 A1 | 12/2008 | Chaiken et al. |
| 2008/0306397 A1 | 12/2008 | Bonmassar et al. |
| 2008/0312560 A1 | 12/2008 | Jamsen et al. |
| 2008/0312709 A1 | 12/2008 | Volpe et al. |
| 2009/0036747 A1 | 2/2009 | Hayter et al. |
| 2009/0062696 A1 | 3/2009 | Nathan et al. |
| 2009/0069709 A1 | 3/2009 | Schmitz et al. |
| 2009/0069722 A1 | 3/2009 | Flaction et al. |
| 2009/0076336 A1 | 3/2009 | Mazar et al. |
| 2009/0171381 A1 | 7/2009 | Schmitz et al. |
| 2009/0192416 A1 | 7/2009 | Ernst et al. |
| 2009/0228068 A1 | 9/2009 | Buhlmann et al. |
| 2009/0247910 A1 | 10/2009 | Klapper |
| 2009/0306741 A1 | 12/2009 | Hogle et al. |
| 2009/0318779 A1 | 12/2009 | Tran |
| 2010/0137748 A1 | 6/2010 | Sone et al. |
| 2010/0152619 A1 | 6/2010 | Kalpaxis et al. |
| 2010/0152622 A1 | 6/2010 | Teulings |
| 2010/0152623 A1 | 6/2010 | Williams |
| 2010/0168559 A1 | 7/2010 | Tegg et al. |
| 2010/0292617 A1 | 11/2010 | Lei et al. |
| 2011/0004207 A1 | 1/2011 | Wallace et al. |
| 2011/0237974 A1 | 9/2011 | Bartol et al. |
| 2012/0053491 A1 | 3/2012 | Nathan et al. |
| 2013/0123659 A1 | 5/2013 | Bartol et al. |

OTHER PUBLICATIONS

Bartol, Stephen MD, and Laschuk, Maria MD, "Use of Nerve Stimulator to Localize the Spinal Nerve Root During Arthroscopic Discectomy Procedures", Canadian Spine Society Meeting, Vernon, BC, Canada, Mar. 2002.

Begg et al. "Computational Intelligence for Movement Sciences: Neural Networks and Other Emerging Techniques" 2006.

Bourke et al. "A Threshold-Based Fall-Detection Algorithm Using a Bi-Axial Gyroscope Sensor" Medical Engineering and Physics 30 (2008) 84-90.

Fee Jr., James W.; Miller, Freeman; Lennon, Nancy; "EMG Reaction in Muscles About the Knee to Passive Velocity, Acceleration, and Jerk Manipulations"; Alfred I. duPont Hospital for Children, Gait Laboratory, 1600 Rockland Road, Wilmington, DE 19899, United States Journal of Electromyography and Kinesiology 19 (2009) 467-475.

Koceja, D.M., Bernacki, R.H. and Kamen, G. "Methodology for the Quantitative Assessment of Human Crossed-Spinal Reflex Pathways," Medical & Biological Engineering & Computing, Nov. 1991, pp. 603-606, No. 6, US.

Tarata, M.; Spaepen, A.; Puers, R.; "The Accelerometer MMG Measurement Approach, in Monitoring the Muscular Fatigue"; Measurement Science Review; 2001; vol. 1, No. 1.

Murphy, Chris; Campbell, Niall; Caulfield, Brian; Ward, Tomas and Deegan, Catherine; "Micro Electro Mechanical Systems Based Sensor for Mechanomyography", 19th international conference Biosignal 2008, Brno, Czech Republic.

Nijsen, Tamara M.E.; Aarts, Ronald M.; Arends, Johan B.A.M.; Cluitmans, Pierre J.M.; "Model for Arm Movements During Myoclonic Seizures"; Proceedings of the 29th Annual International Conference of the IEEE EMBS Cite Internationale, Lyon, France Aug. 23-26, 2007.

Ohta, Yoichi; Shima, Norihiro; Yabe, Kyonosuke; "Superimposed Mechanomyographic Response at Different Contraction Intensity in Medial Gastrocnemius and Soleus Muscles"; International Journal of Sport and Health Science, vol. 5, 63-70, 2007.

ROBOTIC SURGICAL SYSTEM WITH MECHANOMYOGRAPHY FEEDBACK

TECHNICAL FIELD

The present invention relates generally to minimally invasive robotic surgical systems.

BACKGROUND

Robotic surgery involves the use of one or more robotically manipulated surgical instruments, extending within a patient to perform a surgical procedure. Each surgical instrument may include a specially configured end effector disposed on a distal end portion of the instrument to effectuate, for example, a grasping routine. Robotic surgical systems enable minimally invasive surgical procedures to be performed with less trauma to the subject than in traditional surgical procedures, and may potentially have a greater degree of precision.

During a robotically assisted surgical procedure, a surgeon generally oversees the operation of the robotic manipulator in a tele-opritive manner while seated at a master station. The master station may include both specially configured user input controls and a display. Display feedback provided to the surgeon may typically include direct visual feedback, such as from a robotically controlled endoscopic camera that may extend within the patient. From this visual feedback, the surgeon may direct the robotic manipulator to perform the desired task/procedure.

SUMMARY

A robotic surgical system for performing a surgical procedure within the body of a subject includes an elongate surgical instrument, a robotic controller configured to control the motion of the distal end portion of the surgical instrument, and a mechanomyography feedback system in communication with the robotic controller. The mechanomyography feedback system includes an elongate sphincter contraction sensor configured to monitor a physical response of a sphincter of a subject and to provide a mechanomyography signal corresponding to the monitored physical response. Additionally, the feedback system includes a processor configured to receive the mechanomyography signal, to determine if the received signal is indicative of an induced sphincter response, and to provide a control signal to the robotic controller if an induced sphincter response is detected.

In one configuration, the robotic controller may be configured to prevent motion of the distal end portion of the surgical instrument in response to the control signal. In another configuration, the robotic controller may be configured to limit the range of motion of the elongate surgical instrument in response to the received control signal. When the surgical instrument includes an end effector actuatable in at least one degree of freedom, the robotic controller may be configured to prevent actuation of the end effector in response to the control signal.

The control signal may include an indication of a proximity between the distal end of the elongate surgical instrument and a nerve. In response to the detected proximity, the robotic controller may be configured to vary the speed of the distal end of the elongate surgical instrument.

An induced sphincter response may be determined by computing a time derivative of a contact force monitored from the sphincter contraction sensor, and comparing the computed time derivative to a threshold. In an embodiment where the surgical instrument includes a stimulator configured to provide an electrical stimulus, an induced muscle response may include a contraction or relaxation of at least one of an external sphincter of the bladder and an external sphincter of the anus attributable to a depolarization of a sacral nerve innervating the sphincter, wherein the depolarization of the nerve is induced by the provided electrical stimulus.

The robotic surgical system may further include a master station in communication with the robotic controller. The master station may be configured to receive an input from a user corresponding to an intended movement of the distal end of the surgical instrument and to provide a motion command to the robotic controller corresponding to the received input. Additionally, the master station may be configured to provide at least one of a visual alert and auditory alert if an induced muscle response is detected.

A method of nerve avoidance during robotically assisted surgery may include: controlling the motion of a distal end portion of an elongate surgical instrument using a robotic controller; receiving a mechanomyography signal from an elongate sphincter contraction sensor; determining if the received mechanomyography signal is indicative of an induced sphincter response; and providing a control signal to the robotic controller if an induced sphincter response is detected.

The method may further include electronically limiting the range of motion of the distal end portion of the elongate surgical instrument in response to the received control signal. Alternatively, it may include preventing motion of the distal end portion of the surgical instrument in response to the control signal. Where the control signal includes an indication of proximity between the distal end portion and a nerve, the method may include varying the speed of the distal end of the elongate surgical instrument as a function of the indicated proximity.

The above features and advantages and other features and advantages of the present invention are readily apparent from the following detailed description of the best modes for carrying out the invention when taken in connection with the accompanying drawings.

BRIEF DESCRIPTION OF THE DRAWINGS

FIG. 6 is a schematic side-view illustration of a second embodiment of a sphincter contraction sensor.

DETAILED DESCRIPTION

Figure 1:
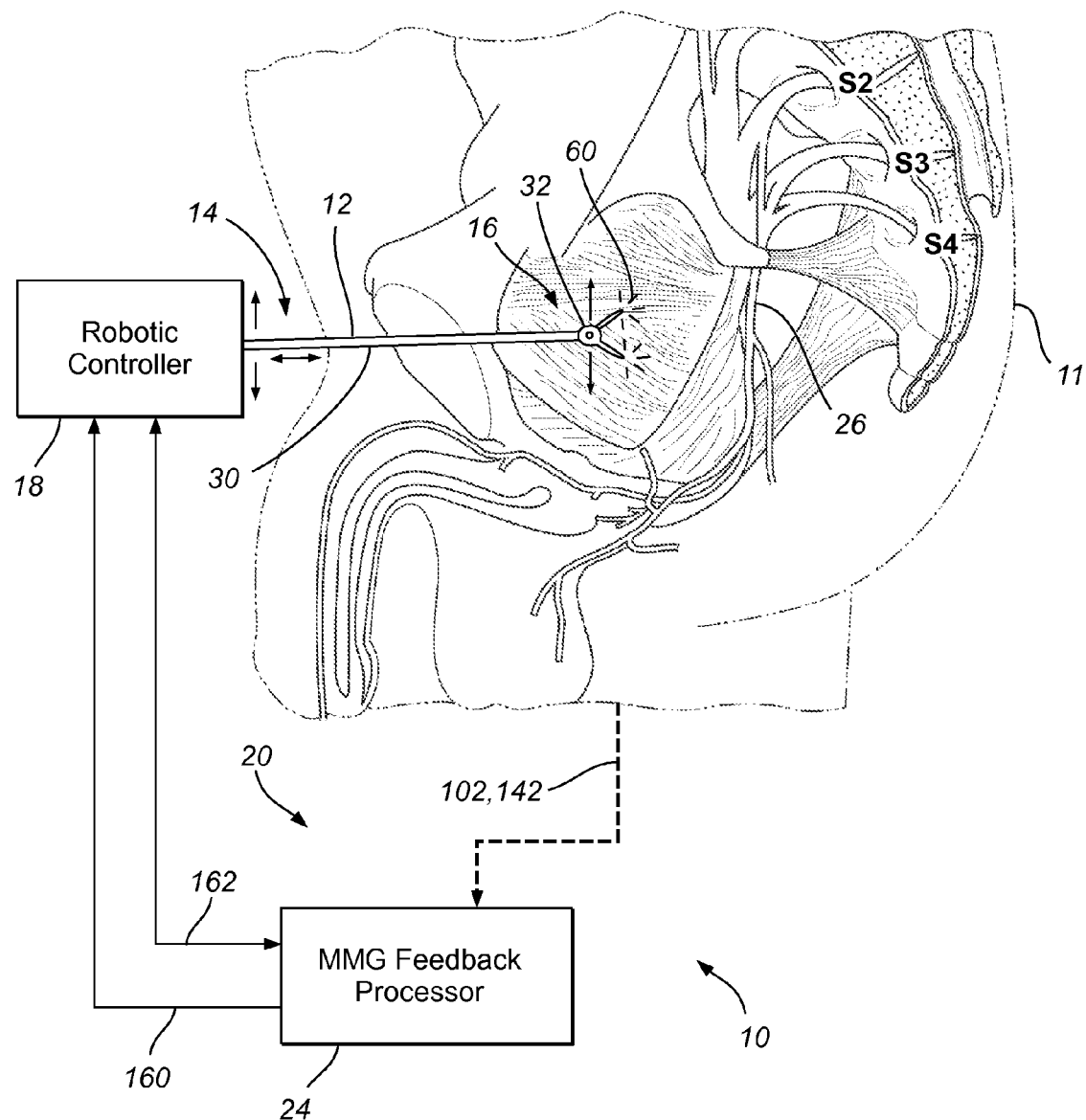
FIG. 1 is a schematic partial cross-sectional illustration of a robotic surgical system being used in a pelvic floor surgical procedure, and providing a stimulus proximate to a sacral nerve of a human subject.

Referring to the drawings, wherein like reference numerals are used to identify like or identical components in the various views, FIG. 1 schematically illustrates a robotic surgical system 10 for performing a surgical procedure within the body of a human subject 11. A similar robotic surgical system is described in U.S. patent application Ser. No. 13/428,693, filed Mar. 23, 2022 (entitled "Robotic Surgical System with Mechnomyography Feedback"), which is hereby incorporated by reference in its entirety.

As illustrated, the robotic surgical system 10 includes an elongate surgical instrument 12 having a proximal end portion 14 and a distal end portion 16, a robotic controller 18 configured to control the motion of the distal end portion 16 of the surgical instrument 12, and a mechanomyography (MMG) feedback system 20 in communication with the robotic controller 18. The elongate surgical instrument 12 and robotic controller 18 may be particularly configured to perform one or more surgical procedures in or around the lower abdomen and/or pelvic floor of the human subject 11. Such procedures may include, for example and without limitation, hernia repair, prostatectomy, hysterectomy, and/or other surgical procedures on the bladder, prostate, colon, pelvis, or other neighboring organs.

Figure 2:
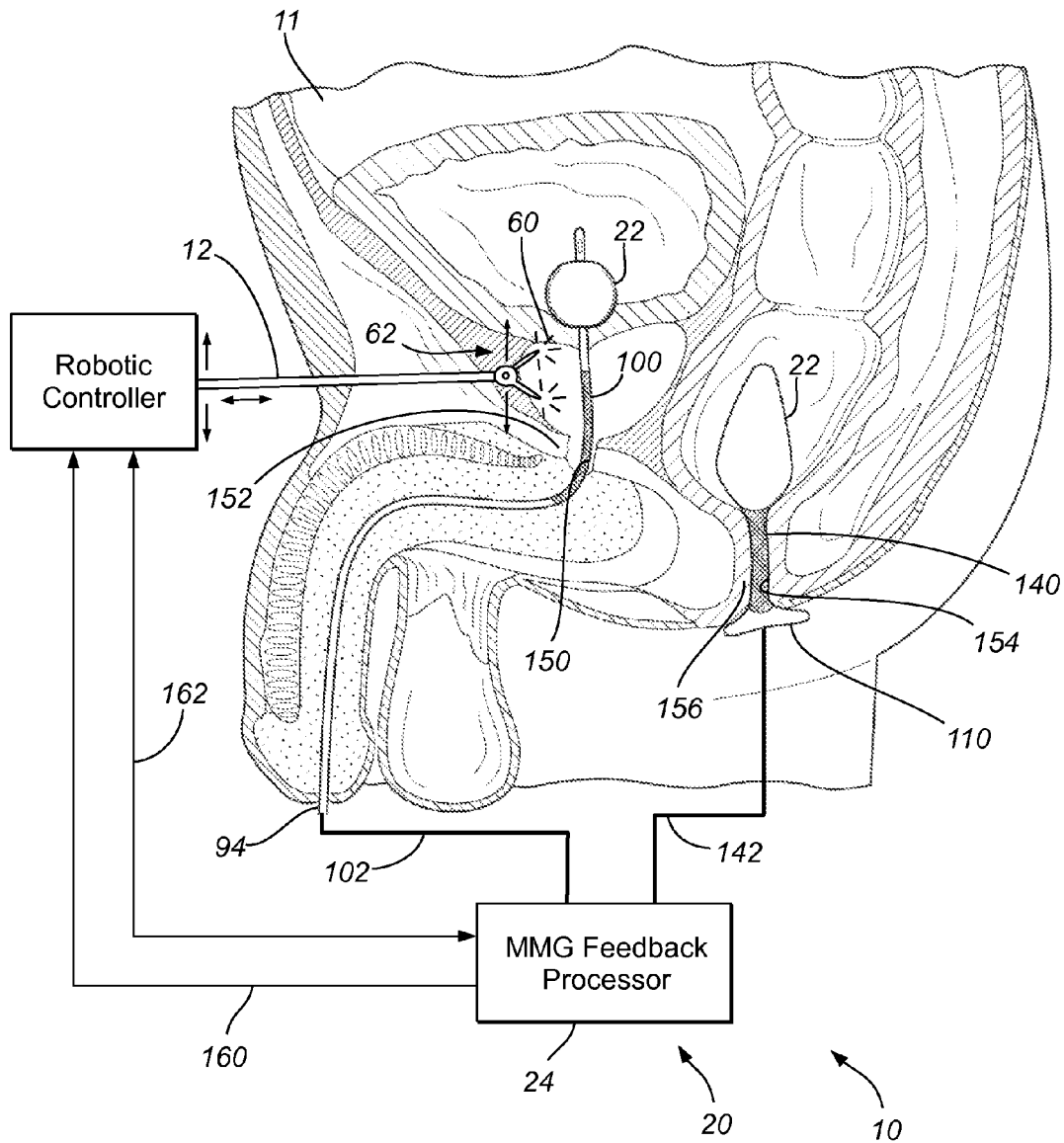
FIG. 2 is a schematic partial cross-sectional illustration of a robotic surgical system of FIG. 1, receiving mechanomyography feedback from a first and second embodiment of a sphincter contraction sensor.

With brief reference to FIG. 2, the MMG feedback system 20 may include at least one mechanical sphincter contraction sensor 22 and an MMG feedback processor 24 in communication with the mechanical sphincter contraction sensor 22. A similar MMG feedback system 20 is described in U.S. patent application Ser. No. 13/591,280, filed Aug. 22, 2022 (entitled "Nerve Monitoring System"), which is hereby incorporated by reference in its entirety.

Referring again to FIG. 1, during a robotic surgical procedure, the MMG feedback system 20 may be particularly configured to detect the presence of one or more sacral nerves 26 within the human subject 11. As used herein, reference to "sacral nerves" generally includes any nerves exiting the sacrum portion of the human spine (e.g., the S2, S3, or S4 vertebrae), such as, for example, the pudendal nerve, the pelvic splanchnic nerve, the inferior hypogastric nerve, the inferior rectal nerve, the pelvic plexus, and/or any other nerve incorporated into the urinary, fecal, and/or sexual functioning of humans.

The pudendal nerve and/or other sacral nerves originating from the sacral plexus include sensory, somatic and autonomic nerves that innervate the external genitalia of both sexes. Additionally, these nerves innervate and control the contractions of the external sphincter of the anus and external sphincter of the bladder. A sphincter is an anatomical structure comprised mainly of circular muscle, which maintains constriction of a natural body passage or orifice and which relaxes as required by normal physiological functioning. During a pelvic floor surgery, for example, these nerves are at a significant risk of being stretched, pinched, torn, or otherwise injured. Any such damage may result in a temporary or permanent loss of nerve signal transmission, and may potentially cause urinary and/or fecal incontinence and/or loss of bowel and/or bladder control.

During a surgical procedure, the surgical instrument 12 may extend through an opening in the body of the subject 11, with the distal end portion 16 disposed within the body of the subject 11, and the proximal end portion 14 disposed outside of the body of the subject 11. In one configuration, the surgical instrument 12 may generally be defined by a rigid elongate body 30, such that movement of the proximal end portion 14 of the instrument 12 may result in a predictable movement of the distal end portion 16 of the instrument 12.

The surgical instrument 12 may further include an end effector 32 disposed at the distal end portion 16. The end effector 32 may be responsible for performing one or more cutting, grasping, cauterizing, or ablating functions, and may be selectively actuatable in at least one degree of freedom (i.e. a movable degree of freedom, such as rotation, or an electrical degree of freedom, such as selectively delivering ablative energy). Additionally, the end effector 32 may be configured to selectively rotate and/or articulate about the distal end portion 16 of the surgical instrument 12 to enable a greater range of motion/dexterity during a procedure.

In one embodiment, such as generally illustrated in FIG. 1, the end effector 32 may be configured to resemble forceps, and may have one or more controllably movable jaws adapted to articulate about a hinged joint. The selective articulation of the one or more jaws may be enabled, for example, by cables or pull wires extending to the robotic controller through the rigid elongate body 30 of the instrument 12.

Figure 3:
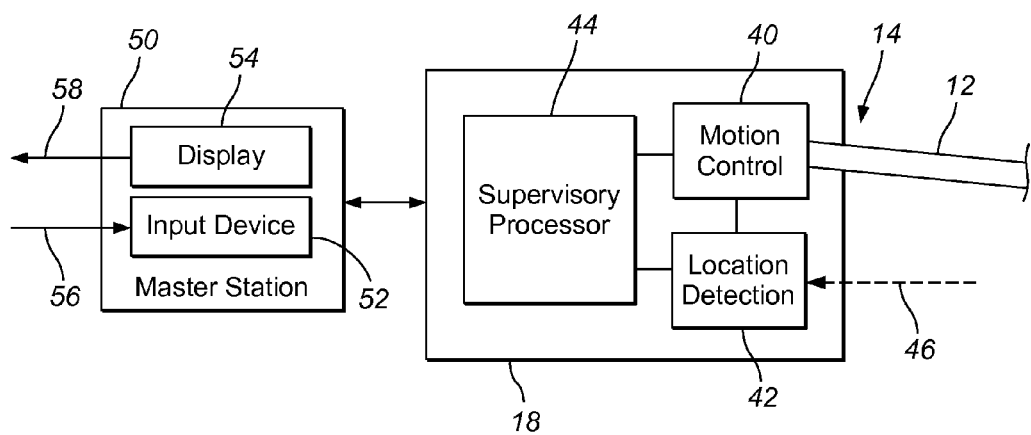
FIG. 3 is a schematic diagram of a robotic controller.

The robotic controller 18 may be responsible for controllably performing a minimally invasive surgical procedure within the body of the subject 11 by controllably manipulating the proximal end 14 of the surgical instrument 12 in a manner that results in a controlled motion of the distal end portion 16. As generally illustrated in FIG. 3, in one configuration, the robotic controller 18 may include a motion controller 40, a location detection module 42 and a supervisory processor 44. The motion controller 40 may include a plurality of motors, linear actuators, or other such components that may be required to manipulate the proximal end 14 of the surgical instrument 12 in six or more degrees of freedom. (e.g., three degrees of translation, three degrees of rotation, and/or one or more degrees of actuation). Additionally, the motion controller 40 may include one or more processors or digital computers and/or power electronics that may be required to convert a received motion command into a physical actuation of a motor or actuator.

The location detection module 42 may include one or more digital computers or processing devices that may be configured to determine the position/motion of the distal end portion 16 of the surgical instrument 12, such as relative to one or more external reference frames. In one configuration, the location detection module 42 may monitor the behavior of the motion controller 40 to determine the motion of the distal end portion 16 using kinematic relationships of the surgical instrument 12. In another configuration, the location detection module 42 may receive a location signal 46 from an external, positioning system (not shown), which may resolve the position of the distal end portion 16 of the surgical instrument 12 using, for example, ultrasound energy, magnetic energy, or electromagnetic energy that may be propagated through the subject 11.

The supervisory processor 44 may be embodied as one or more digital computers or data processing devices, each having one or more microprocessors or central processing units (CPU), read only memory (ROM), random access memory (RAM), electrically-erasable programmable read only memory (EEPROM), a high-speed clock, analog-to-digital (A/D) circuitry, digital-to-analog (D/A) circuitry, input/output (I/O) circuitry, power electronics/transformers, and/or signal conditioning and buffering electronics. The individual control routines/systems resident in the supervisory processor 44 or readily accessible thereby may be stored in ROM or other suitable tangible memory location and/or memory device, and automatically executed by associated hardware components of the processor 44 to provide the respective control functionality. In one embodiment, the supervisory processor 44 may provide the motion controller 40 with actuation commands in a closed loop manner using the positional feedback provided by the location detection module 42. The supervisory processor 44 may perform any combination of feedforward, feedback, and/or predictive control schemes to accurately control the motion and/or actuation of the distal end portion 16 of the surgical instrument 12.

Additionally, the robotic controller 18 may be in communication with a master station 50 that includes a user input device 52 and a user feedback device such as a display 54. The user input device 52 may receive an input 56 from a user that corresponds to an intended movement of the distal end portion 16 of the surgical instrument 12. The master station 50 may then provide a motion command to the robotic controller 18 that corresponds to the received input 56. Similarly, the master station 50 may receive visual information 58 from the robotic controller and convey it to the user via the display 54.

While FIG. 3 provides one embodiment of a robotic controller 18, other embodiments, configurations, and or control schemes may similarly be used to manipulate the surgical instrument 12 in a manner that results in a controlled, and intended motion of the distal end portion 16. While the robotic controller 18 and surgical instrument 12 described above are generally of the kind used for robotic laparoscopy, such description is made for illustrative purposes and should not be limiting. Other minimally invasive surgical systems that employ a robotic controller 18 to control the motion of the distal end of an elongate surgical instrument may include, for example, robotic catheter systems and/or robotic endoscopic systems.

Referring again to FIGS. 1 and 2, the robotic controller 18 may be in communication with the MMG feedback system 20. As described above, the MMG feedback system 20 may include at least one sphincter contraction sensor 22 and an MMG feedback processor 24 in communication with the sphincter contraction sensor 22. The MMG feedback system 20 may provide the robotic controller 18 with an awareness of one or more sacral nerves 26 that may be adjacent to the distal end portion 16 of the surgical instrument 12. In this manner, the robotic system 10 may avoid manipulating tissue (either through translational motion or actuation of an end effector 32) that may jeopardize neural integrity.

As generally illustrated in FIG. 2, and as will be discussed in greater detail below, a sphincter contraction sensor 22 may be configured to be placed in mechanical communication with the external sphincter of the bladder and/or the external sphincter of the anus such that it may be capable of monitoring physical contractions and/or relaxations of the respective sphincters.

During a surgical procedure, the elongate surgical instrument 12 may emit a stimulus 60 (e.g. an electrical stimulus 60) within an intracorporeal treatment area 62 of the subject 11, where one or more sacral nerves 26 are expected to exist. As used herein, the "intracorporeal treatment area" specifically refers to a surgical treatment area within the body of the subject 11 (i.e., sub-dermis). While described as an "electrical stimulus 60," the stimulus 60 may alternatively include, for example, a thermal, chemical, ultrasonic, or infrared stimulus.

Referring to FIGS. 1 and 2, if the electrical stimulus 60 is provided at, or sufficiently close to a sacral nerve 26 within the treatment area 62, the stimulus 60 may be received by the nerve 26 in a manner that causes the nerve to depolarize. A depolarizing nerve may then induce a response in a muscle (sphincter) that is innervated by the nerve 26. One form of an evoked muscle response may manifest itself as a contraction and/or relaxation of one or both of the external sphincter of the anus and external sphincter of the bladder. Likewise, another evoked muscle response may manifest itself as a contraction and/or relaxation of one or both of the internal sphincter of the anus and internal sphincter of the bladder. As will be discussed below, by placing a suitable force sensor within the sphincter, the MMG feedback system 20 may be capable of correlating an induced/involuntary sphincter response (i.e., contraction or relaxation), with the electrical stimulus 60 provided to the treatment area 62.

Figure 4:
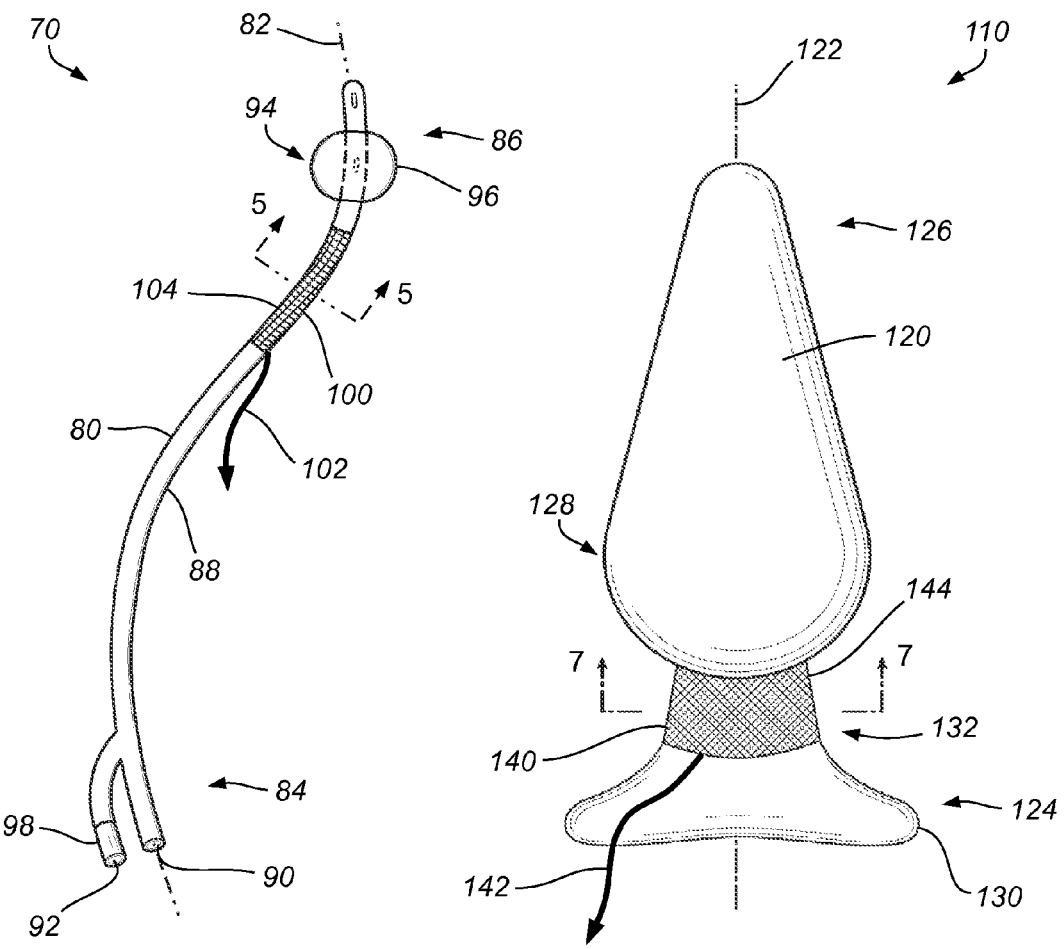
FIG. 4 is a schematic perspective illustration of a first embodiment of a sphincter contraction sensor.

FIGS. 4 and 6 illustrate two potential embodiments of a sphincter contraction sensor 70, 110 (respectively). As shown, the sphincter contraction sensor 70 provided in FIG. 4 may be particularly suited for monitoring a contraction of the external sphincter of the bladder, while the sphincter contraction sensor 110 provided in FIG. 6 may be particularly suited for monitoring a contraction of the external sphincter of the anus (i.e., a "bladder sphincter contraction sensor 70" and an "anal sphincter contraction sensor 110", respectively). Each sphincter contraction sensor 70, 110 may be of a size and/or dimension to be inserted within an orifice defined by the respective sphincter. Likewise, each sphincter contraction sensor 70, 110 may be particularly configured to measure a physical response of the sphincter. The physical response may include a physical/mechanical contraction or relaxation of the sphincter; though, as used herein, a physical response should be viewed as distinct from an electrical and/or biochemical response (even if the various response-types may be inter-related under certain circumstances).

Referring to FIG. 4, one configuration of a bladder sphincter contraction sensor 70 may include an elongate device body 80 disposed along a longitudinal axis 82. The elongate device body 80 may include a proximal end portion 84 and a distal end portion 86, with the distal end portion being configured for insertion into the human subject 11. In one configuration, the elongate device body 80 may be a Foley Catheter. As used in the art, a Foley Catheter is a flexible tube 88 that may be passed through the urethra of a subject and into the bladder.

The flexible tube 88 may internally define two separated channels, or lumens that extend the length of the tube 88 along the longitudinal axis 82. A first lumen 90 may be open at both ends, and may be configured to allow urine to freely pass from the bladder into a collection bag. The second lumen 92 may be in fluid communication with an inflatable bulbous retention feature 94 (i.e., a balloon 96) disposed at the distal end portion 86 of the device body 80. Using the second lumen 92, the balloon 96 may be inflated with a sterile water and/or saline solution once inside the bladder to restrain the device body 80 from withdrawing from the bladder through the sphincter. The second lumen 92 may include a valve 98 at the proximal end portion 84 of the device body 80, which may restrict the flow of the sterile water out of the balloon 96.

The bladder sphincter contraction sensor 70 may further include a force sensor 100 in mechanical communication with the elongate device body 80 at a position along the longitudinal axis 82 where it may monitor a contraction of a sphincter against the device body 80. In one configuration, the force sensor 100 may be disposed at or near the distal end portion 86 of the elongate device body 80, though may be proximally located relative to the bulbous retention feature 94.

When in place within the sphincter of the subject, the force sensor 100 may be configured to generate a mechanomyography output signal 102 in response to a contact force applied against the elongate device body 80 by the tissue of the sphincter. For example, in one configuration, the force sensor 100 may include a pressure sensitive film 104 that may be circumferentially disposed about a portion of the device body 80. In other configurations, the force sensor 100 may include one or more strain gauges, piezoresistive strain gauges, capacitive force sensors, piezoelectric strain gauges, pneumatic pressure transducers, optical force transducers (e.g., fiber Bragg grating sensors), or any other known or hereinafter developed force sensors that may generate an output signal 102 in response to a contact force applied against the elongate device body 80. Likewise, the force sensor 100 may be disposed about the device body 80 in any orientation such that it can monitor a contact force applied against the elongate device body 80. For example, in one configuration the force sensor 100 may be circumferentially disposed about the device body 80, as mentioned above; in another configuration, however, the force sensor 100 may radially extend within the device body 80.

The mechanomyography output signal 102 may include one or more of a variable voltage signal, a variable current signal, a variable resistance, an analog pressure map, and/or a digital pressure map. Regardless of the form of the signal, the mechanomyography output signal 102 may correspond to either a magnitude or a change in magnitude of a contact force applied against the elongate device body 80 by the tissue of the sphincter.

Figure 5:
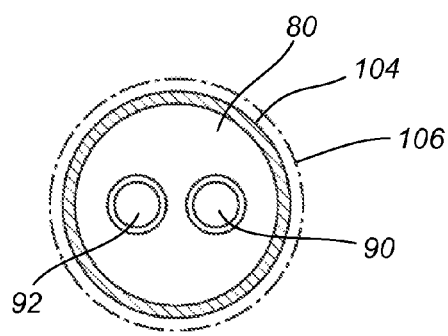
FIG. 5 is a schematic cross-sectional view of the sphincter contraction sensor of FIG. 4, taken along line 5-5.

FIG. 5 illustrates a schematic cross-sectional view of the bladder sphincter contraction sensor 70 shown in FIG. 4, taken along line 5-5. In this configuration, the contraction sensor 70 includes a generally circular device body 80 that defines a first lumen 90 and a second lumen 92. In this configuration, a pressure sensitive film 104 is circumferentially disposed about the device body 80, however, in other configurations, one or more discrete force sensors 100 may be disposed at various locations around the circumference of the device body 80. Finally, the bladder sphincter contraction sensor 70, may include a bio-compatible laminate 106 circumferentially disposed about the pressure sensitive film 104. Such a laminate 106 may be sufficiently thin to avoid altering the pressure-transducing functions or sensitivity of the film 104, however, it may act as a fluid barrier to allow proper functioning of the film 104.

FIG. 6 illustrates one configuration of an anal sphincter contraction sensor 110. Similar to the bladder sphincter contraction sensor 70, the anal sphincter contraction sensor 110 may include an elongate device body 120 disposed along a longitudinal axis 122. The elongate device body 120 may include a proximal end portion 124 and a distal end portion 126, wherein the distal end portion is configured for insertion into the human subject 11. As may be appreciated, the elongate device body 120 of the anal sphincter contraction sensor 110 may be particularly suited for insertion into the anus and/or rectal cavity of the subject 11, and may comprise an intra-anal plug. In other embodiments, the anal sphincter contraction sensor 110 may more closely resemble an elongate catheter.

As shown, in one configuration, the elongate device body 120 may include a bulbous retention feature 128 at the distal end portion 126, and may include a flared feature 130 at the proximal end portion 124. Furthermore, a necked portion 132 may be disposed between the proximal end portion 124 and the distal end portion 126. The necked portion 132 may have a narrower diameter than both the bulbous retention feature 128 and the flared feature 130. In this manner, upon insertion into the orifice defined by the anal sphincter, the anal sphincter may locate about the necked portion 132, where the bulbous retention feature 128 may restrain the device body 120 from being expelled from the subject, and the flared feature 130 may restrain the device body 120 from fully passing into the subject.

The anal sphincter contraction sensor 110 may further include a force sensor 140 in mechanical communication with the elongate device body 120 at a position along the longitudinal axis 122 where it may monitor a contraction of the anal sphincter against the device body 120. In one configuration, the force sensor 140 may be disposed at or near the necked portion 132 of the elongate device body 120, (i.e., proximal to the bulbous retention feature 128, and distal to the flared feature 130).

When in place within the sphincter of the subject, the force sensor 140 may be configured to generate a mechanomyography output signal 142 in response to a contact force applied against the elongate device body 120 by the tissue of the sphincter. For example, in one configuration, the force sensor 140 may include a pressure sensitive film 144 that may be circumferentially disposed about the necked portion 132 of the device body 120. In other configurations, the force sensor 140 may include one or more strain gauges, pneumatic pressure transducers, optical force transducers, or any other known or hereinafter developed force sensors that may generate an output signal 142 in response to a contact force applied against the elongate device body 120. The mechanomyography output signal 142 may be similar in nature to the mechanomyography output signal 102 described above, and may include one or more of a variable voltage signal, a variable current signal, a variable resistance, an analog pressure map, and/or a digital pressure map. Regardless of the form of the signal, the mechanomyography output signal 142 may correspond to either a magnitude or a change in magnitude of a contact force applied against the elongate device body 120 by the tissue of the sphincter.

Figure 7:
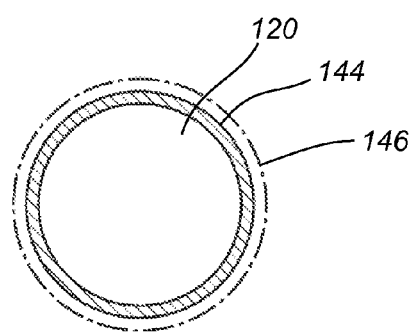
FIG. 7 is a schematic cross-sectional view of the sphincter contraction sensor of FIG. 6, taken along line 7-7.

FIG. 7 illustrates a schematic cross-sectional view of the anal sphincter contraction sensor 110 shown in FIG. 6, taken along line 7-7. In this configuration, the contraction sensor 110 includes a generally circular device body 120, and a pressure sensitive film 144 circumferentially disposed about the device body 120. In other configurations, instead of the film 144, one or more discrete force sensors 140 may be disposed around the circumference of the device body 120. Finally, the anal sphincter contraction sensor 110, may include a bio-compatible laminate 146 circumferentially disposed about the pressure sensitive film 144. Such a laminate 146 may be sufficiently thin to avoid altering the pressure-transducing functions or sensitivity of the film 144, however, it may act as a fluid barrier to allow proper functioning of the film 144.

Referring again to FIG. 2, the human subject 11 is schematically illustrated with both the bladder sphincter contraction sensor 70 and anal sphincter contraction sensor 110 in an operational position within the subject 11. As shown, the bladder sphincter contraction sensor 70 is disposed within an orifice 150 defined by the external sphincter of the bladder 152, and the anal sphincter contraction sensor 110 is disposed within an orifice 154 defined by the external sphincter of the anus 156. Each sphincter contraction sensor 70, 110 includes a respective force sensor 100, 140 configured to be positioned in direct physical contact within the respective sphincter 152, 156. As described above, the respective force sensors 100, 140 may each generate a mechanomyography output signal 102, 142 in response to any sensed contact force by the sphincter against the sensors 70, 110.

Depending on the particular nature of the procedure, the neural monitoring system 10 may be fully operational using either of the two sphincter contraction sensors 70, 110, individually. Alternatively, a surgeon may choose to implement the system 10 using both contraction sensors 70, 110 together.

When both sphincter contraction sensors 70, 110 are used, each contraction sensor 70, 110 may be in respective electrical or wireless communication with the MMG feedback processor 24. In this manner, the MMG feedback processor 24 may be configured to receive the mechanomyography output signal 102 from the bladder sphincter contraction sensor 70 and the mechanomyography output signal 142 from the anal sphincter contraction sensor 110. As will be explained below, the MMG feedback system 20 may be configured to provide one or more control signals 160 to the robotic controller 18 based on at least a portion of the output signals 102, 142 received from one or both sphincter contraction sensors 70, 110.

Figure 8:
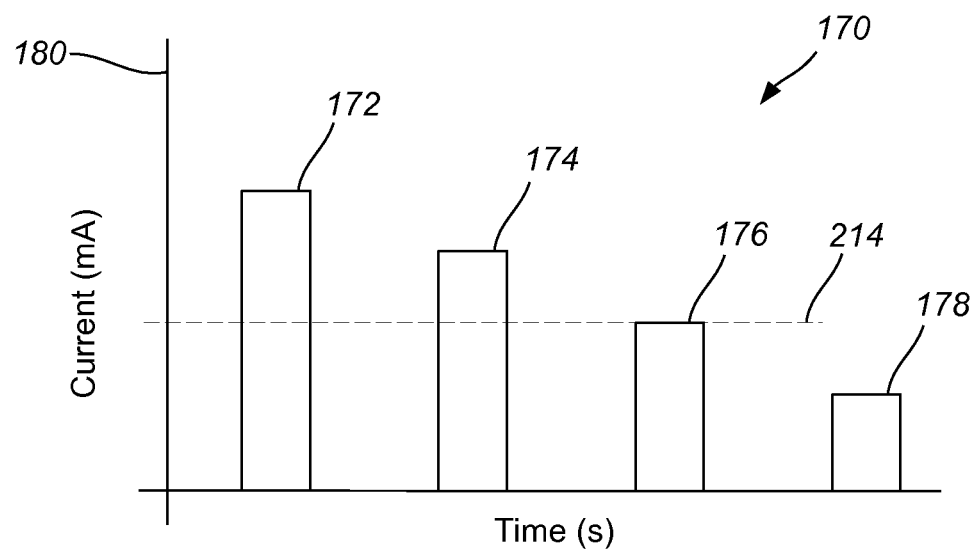
FIG. 8 is a schematic graph of a plurality of electrical stimulus pulses that may be provided to an intracorporeal treatment area of a subject, with stimulus current shown as a function of time.

During the neural testing/detection process, the MMG feedback processor 24 may be in communication with both the robotic controller 18 and one or both sphincter contraction sensors 70, 110. As such, the MMG feedback processor 24 may receive an indication 162 from the robotic controller 18 when an electrical stimulus 60 is transmitted to the tissue and/or nerves residing within the tissue. FIG. 8 generally illustrates a current plot 170 of an electrical stimulus 60 provided to the subject 11. As shown, the electrical stimulus 60 may include a plurality of sequentially administered pulses 172, 174, 176, 178 (e.g., at a 0.5-2.0 Hz frequency). Depending on the application, each pulse may be provided at a different electrical current magnitude 180. Also, while FIG. 8 illustrates direct current (DC) stimulus pulses, the pulses may alternatively be alternating current (AC) pulses, each potentially being provided at a varying root-mean-squared (RMS) current.

Figure 9:
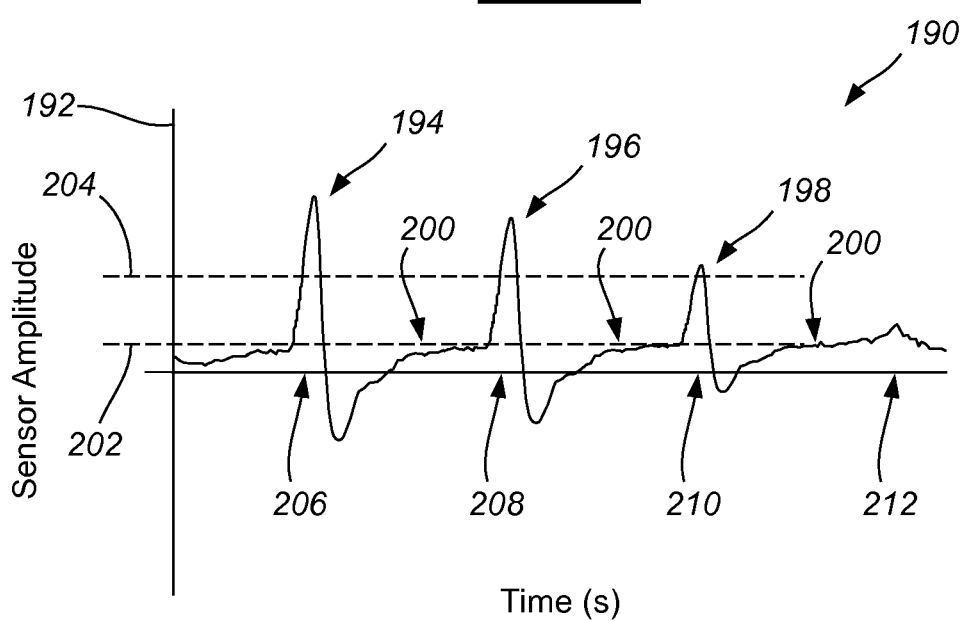
FIG. 9 is a schematic graph of a plurality of sphincter contraction responses that may be sensed in response to the transmission of the plurality of electrical stimulus pulses provided in FIG. 8.

FIG. 9 then illustrates a graph 190 of a sphincter contraction force amplitude 192 vs. time, that may be representative of a contact force applied by the sphincter tissue against the sphincter contraction sensors 70, 110, and which may be conveyed to the processor 24 via one of the mechanomyography output signals 102 and/or 142. The sphincter contraction force 192 illustrated in FIG. 9 may be representative of a sphincter response following the delivery of an electrical stimulus 60 of the type provided in FIG. 8. The sensed sphincter contraction force amplitude 192 may correspond to a plurality of detected sphincter contractions 194, 196, 198 and a plurality of relaxed states 200. As may be appreciated, the "relaxed" states 200 may be representative of a baseline contact force 202 that exists due to the automatic contraction of the sphincter. From this baseline 202, any somatic change in contraction force may cause the sphincter to either contract or relax, depending on the nerve involved (for simplicity, any somatic change in sphincter contraction (i.e., a somatic contraction or a somatic relaxation) will be generally referred to as a sphincter contraction).

In one configuration, a sphincter contraction may be detected by comparing the sensed sphincter contraction force 192 to a threshold 204. The threshold 204 may be dynamically set relative to a baseline (relaxed) contact force 202. As such, the MMG feedback processor 24 may first examine the mechanomyography output signal 102, 142 to determine if a sphincter contraction/relaxation event has occurred. To accomplish this, the MMG feedback processor 24 may compare any change in the sensed sphincter contraction force 192 to the baseline (automatic) contact force 202, which may be continuously updated. If the magnitude of the change exceeds a threshold amount of change, than the MMG feedback processor 24 may indicate that a somatic contraction/relaxation has occurred. While shown in FIG. 9 as a positive threshold 204 relative to the baseline 202, it should also be understood that an induced response may involve a relaxation of the sphincter. As such, a similar negative threshold (not shown) may also be applied below the baseline to monitor for an induced relaxation.

The MMG feedback processor 24 may use internal control logic to determine that a detected sphincter contraction was induced and/or was involuntary (such as generally at 206, 208, 210). In one configuration, this determination may be made by coordinating the sensed response with administered pulses 172, 174, 176 in time. As further shown, the sensor response generally at 212, following pulse 178 may neither register as a sphincter contraction, nor may have a steep enough response to be viewed as "induced." Such a result may be attributable to the current magnitude 180 of the pulse 178 being below a threshold current level 214 that would cause the nerve 26 to begin depolarizing given the distance between the distal end 16 of the elongate device 12 and the nerve 26.

Figure 10:
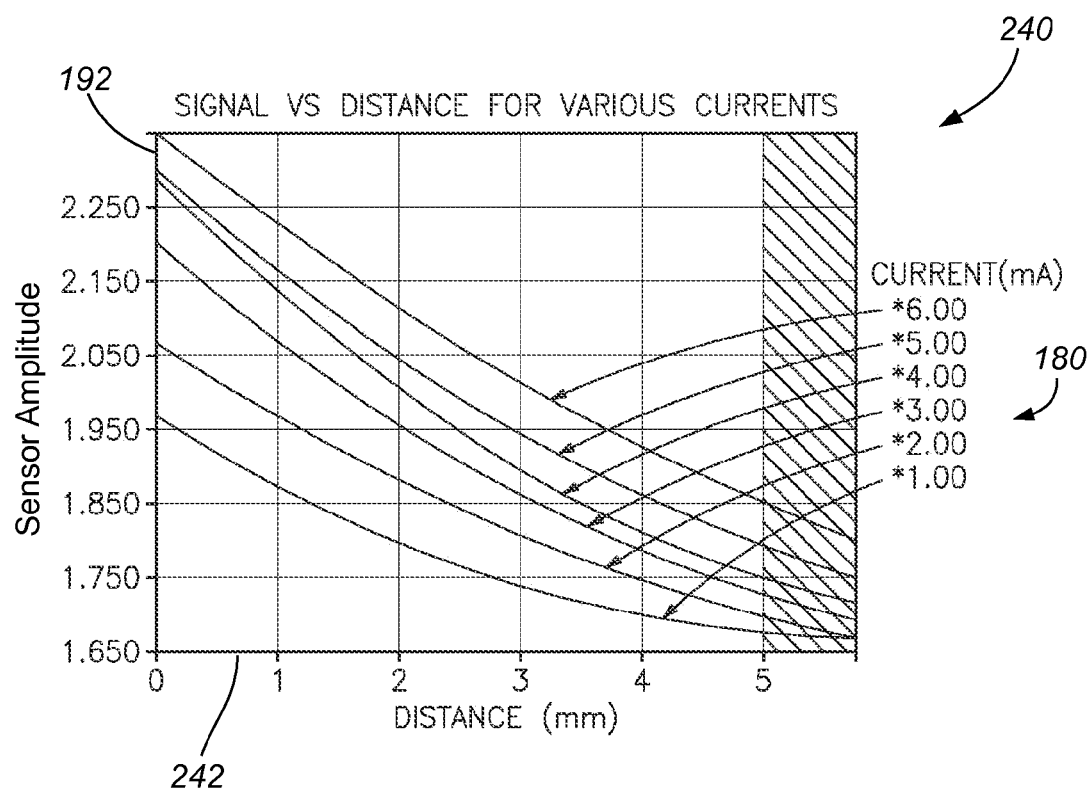
FIG. 10 is a schematic graphic representation of a look-up table that may be used to determine nerve proximity from the distal end portion of a stimulator probe, given a known electrical stimulus amplitude, and a sensed sphincter contraction amplitude.

FIGS. 8 and 9 further illustrate the correlation between the provided current 180 of the electrical stimulus 60, and the amplitude 192 of the monitored sphincter contraction/contact force, given a fixed distance between the distal end portion 16 of the elongate device 12 and the nerve 26. FIG. 10 graphically illustrates an example (i.e., a graph 240) of the interrelation of monitored contact force amplitudes 192, electrical stimulus current levels 180, and distances 242 between the distal end portion 16 of the elongate device 12 and the nerve 26. The MMG feedback processor 24 may maintain this interrelation (e.g., graph 240) as a lookup table within memory associated with the processor 24. In this manner, the MMG feedback processor 24 may determine the proximity (i.e., distance 242) between the distal end portion 16 of the elongate device 12 and the nerve 26, by selecting the distance 242 from table 240, given its knowledge of the current magnitude 180 and sensed contact force amplitude 192.

As generally mentioned above, the MMG feedback processor 24 may include various means to determine if a sensed sphincter contraction (as conveyed by the mechanomyography output signal 102, 142) corresponds to, or was induced by a an electrical stimulus 60 provided by the robotic controller 18. While coordination in time may be one way of accomplishing such a correlation, it may be similarly possible to identify an induced/involuntary contraction by examining one or more response properties of the mechanomyography output signal 102, 142. For example, the speed of the response/contraction may be one parameter that may suggest an induced response. Likewise, an acceleration of the response and/or a time derivative of the acceleration may be monitored to suggest an induced/involuntary response. In each of the three derivatives of contact force (speed, accel., and da/dt), an induced response generally has a greater magnitude than a patient-intended response. In this manner, the MMG feedback processor 24 may be configured to compute one or more time derivatives of the monitored contact force from the received mechanomyography output signal 102, 142. The MMG feedback processor 24 may then compare the computed time derivative of the contact force to a threshold, and determine that mechanomyography output signal 102, 142 corresponds to the electrical stimulus 60 provided by the robotic controller 18 if the time derivative of the contact force exceeds the threshold.

Figure 11:
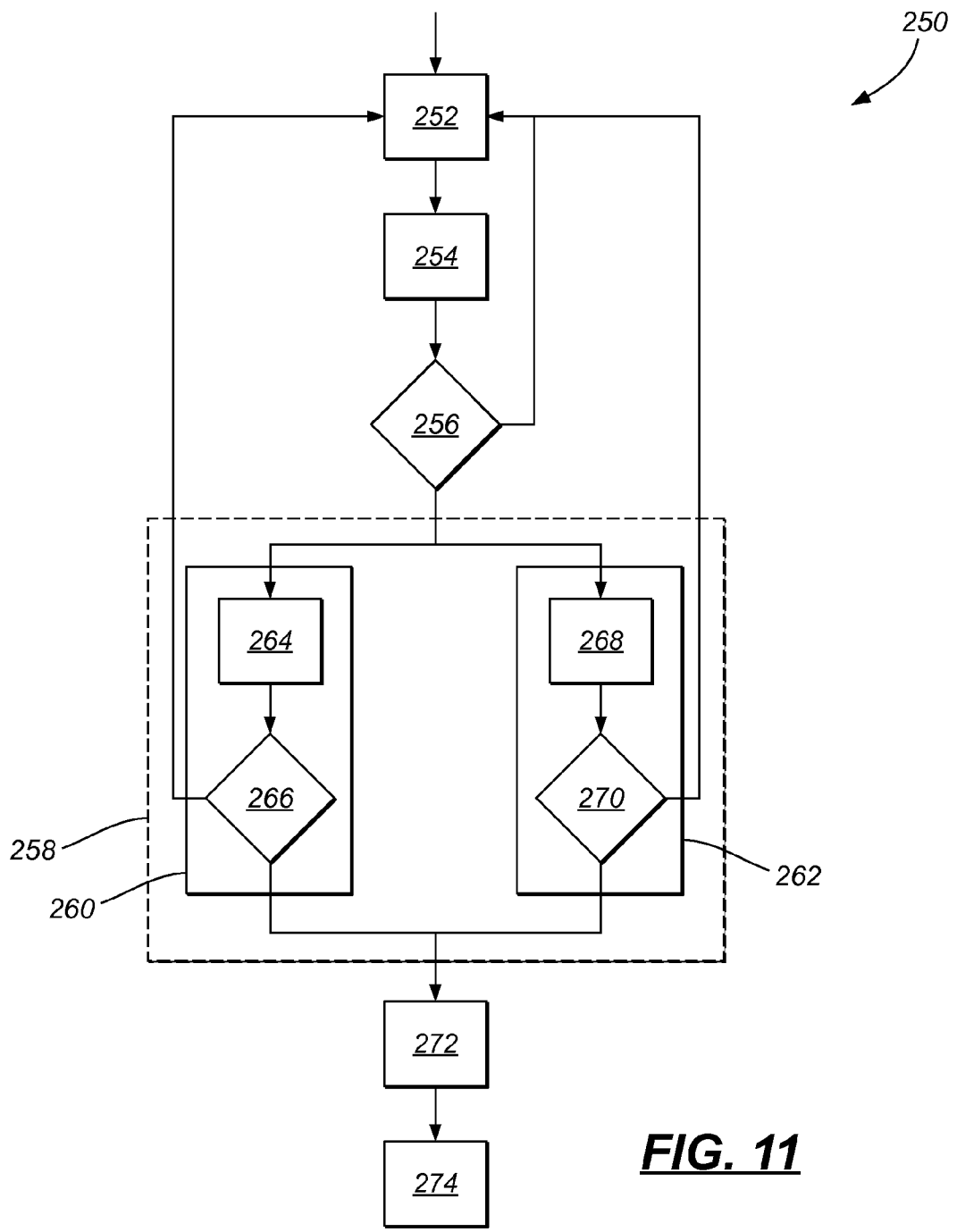
FIG. 11 is a schematic flow diagram of a method of detecting an induced sphincter contraction using a neural monitoring system.

FIG. 11 illustrates one embodiment of a method 250 of detecting an inducted sphincter contraction using a MMG feedback system 20 of the kind described above. The method 250 begins by physically monitoring a contraction of at least one of the external sphincter of the bladder and the external sphincter of the anus using a force sensor disposed within an orifice defined by the respective sphincter (at 252). Step 252 may be performed by an elongate sphincter contraction sensor that includes an elongate device body and a force sensor in mechanical communication with the elongate device body. The contraction monitoring accomplished in step 252 may include generating a mechanomyography output signal in response to a contact force of the sphincter against the force sensor and/or device body.

An MMG feedback processor 24 may then continuously monitor the mechanomyography output signal in step 254 to detect a sphincter contraction. The processor 24 may determine the existence of the sphincter contraction, for example, by calculating a change in magnitude of the mechanomyography output signal over a discrete period of time. If the change in magnitude exceeds a particular threshold (at 256), the processor 24 may then attempt to determine if the detected sphincter contraction was induced by a surgeon-provided stimulus (at 258). If the change in magnitude does not exceed the threshold, the sensor 22/processor 24 may continue monitoring the sphincter response.

As described above, the processor 24 may be configured to determine that a detected sphincter contraction was induced by a surgeon-provided stimulus by either coordinating the response in time with a provided stimulus (at 260), or by further examining properties of the mechanomyography output signal (at 262). In some configurations, the processor 24 may use both time coordination 260 and signal properties 262 to detect an induced response.

To coordinate the response in time with a provided stimulus 260, the processor 24 may first receive an indication that a stimulus was administered to a treatment area of the subject (at 264). It may subsequently calculate the difference in time between when the stimulus was administered and when the response was detected (i.e., when the change in magnitude exceeded the threshold). If the calculated time is below a threshold amount of time (at 266), then the processor 24 may conclude that the detected response was induced by the electrical stimulus, otherwise, it may reject the response as not being temporally relevant.

Further examining properties of the mechanomyography output signal to detect an induced response (at 262) may include computing one or more time derivatives of the mechanomyography output signal (at 268), and comparing the computed time derivative(s) to a threshold (at 270). If a computed time derivative exceeds the threshold, then the processor 24 may conclude that the detected response was an involuntary and/or was an induced response to the electrical stimulus, otherwise, it may reject the response as not being of the kind/nature that is expected to occur in response to an administered stimulus and/or an induced depolarization of the nerve.

Once an induced response is detected/determined, the processor 24 may estimate a distance between the distal end portion of the stimulator probe and the nerve using the magnitude of the current of the applied stimulus and the change in magnitude of the mechanomyography output signal (at 272). For example, the processor 24 may use the two known values (stimulus amplitude and contraction response) to select a distance from a two-dimensional lookup table.

The processor 24 may then provide an indicator to the robotic controller (at 274) that may indicate an induced/involuntary sphincter contraction was detected and/or may indicate an estimated proximity between the distal end portion of the stimulator probe and the nerve.

While FIG. 11 illustrates one potential method 250 of detecting an induced sphincter contraction using an MMG feedback system 20, this method 250 should be illustrative, as other methods may likewise be available.

Referring again to FIGS. 1 and 2, if the MMG feedback system 20 detects an induced response via the sphincter contraction sensor 22, the MMG feedback processor 24 may then provide a control signal 160 to the robotic controller 18. The control signal 160 may include an indication that an induced muscle response was detected, and/or may further include an indication of proximity between the distal end portion 16 of the surgical instrument 12 and a depolarized nerve.

Upon receipt of a control signal 160, the robotic controller 18 may artificially constrain the motion of the distal end portion 16 of the surgical instrument 12 to avoid inadvertent contact with a proximate nerve. For example, in one configuration, the robotic controller 18 may be configured to prevent all motion of the distal end portion 16 of the surgical instrument 12 in response to the received control signal 160. As such, if the distal end portion 16 was in motion, the received control signal 160 may cause the controller 18 to halt such motion and await a further command from the user. Additionally, the robotic controller 18 may be configured to limit or prevent actuation of an end effector 32 upon receipt of the control signal 160. Conversely, in certain therapeutic procedures, the robotic controller 18 may be configured to actuate the end effector 32 upon receipt of the control signal 160 (e.g., selectively deliver ablative energy to tissue proximate to the nerve).

Figure 12:
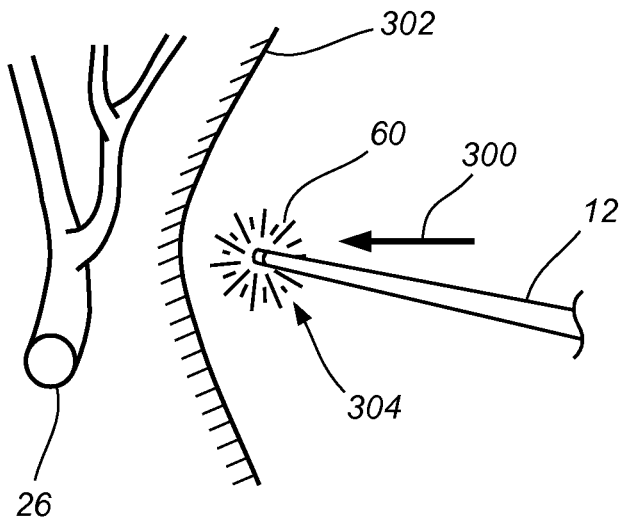
FIG. 12 is a schematic view of a distal end portion of an elongate surgical instrument moving with respect to a nerve of a subject.

In another configuration, such as schematically illustrated in FIG. 12, upon receipt of the control signal 160, the robotic controller may note the direction 300 of current motion of the surgical instrument 12, and may limit further instrument motion in that direction 300 (or directions with a component vector substantially aligned with the direction 300 of motion).

Figure 13:
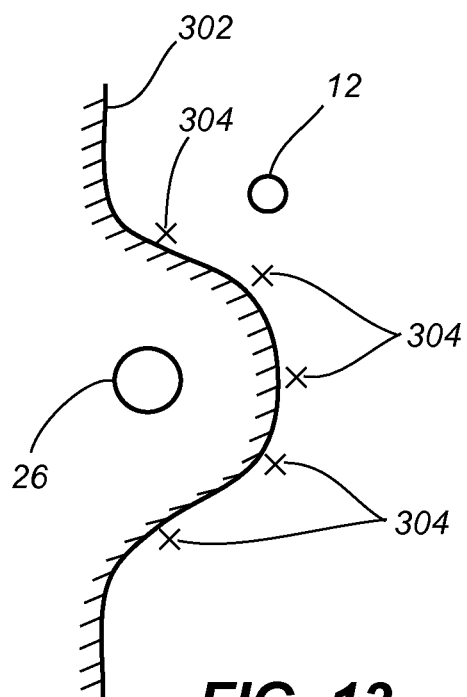
FIG. 13 is a schematic view of FIG. 12, with a virtual barrier being erected about the nerve.

In still another configuration, the robotic controller 18 may construct a virtual barrier 302 based on the direction of motion of the surgical instrument 12, and the location 304 of the instrument 12 when the control signal 160 was received. The virtual barrier 302 may be maintained in an associated memory of the robotic controller 18, and may limit the allowed range of motion of the surgical instrument 12, such that the surgical instrument 12 is artificially restricted from crossing the virtual barrier 302. As generally illustrated in FIG. 13, as the surgical instrument 12 moves, the virtual barrier 302 may be refined according to the receipt of successive control signals 160/locations 304.

Once a nerve is detected, the robotic controller 18 may be configured to vary the permitted speed of the distal end portion 16 of the surgical instrument 12 as a function of the indicated proximity between the real-time location of the instrument 12 and the estimated position of the nerve. As such, the instrument 12 may be allowed to move more quickly and/or at a higher rate of speed when it is farther from the nerve. In this manner, the precision of the movements may be enhanced as one or more nerves become more proximate.

If the presence of a proximate nerve is detected (via an induced sphincter contraction), and/or if an action is performed by the robotic controller 18 to adjust or limit the allowed motion of the surgical instrument 12, the robotic controller 18 may likewise transmit an alert (i.e., a visual alert or an auditory alert) to the user via the master station 50.

Using the system described above, robotic, minimally invasive surgery may be performed in a manner that may allow a surgeon to be aware of nerves/nerve roots that may lie within the treatment area. This is important because neural tissue may often be visually indistinguishable from surrounding tissue, thus traditional visual methods of guidance and control may be ineffective. In this manner, using the above-described system, care may be taken to avoid manipulating neural tissue (either intentionally or inadvertently) in a manner that may injure one or more nerves and/or result in long-term paralysis. Said another way, the described system may allow the user and/or robotic controller to "see" the nerves within the treatment area using a non-visual and/or indirect sensing means. Once their presence is identified, appropriate care may be taken to avoid inadvertent or unintended contact with them.

While the best modes for carrying out the invention have been described in detail, those familiar with the art to which this invention relates will recognize various alternative designs and embodiments for practicing the invention within the scope of the appended claims. It is intended that all matter contained in the above description or shown in the accompanying drawings shall be interpreted as illustrative only and not as limiting.

The invention claimed is:

1. A robotic surgical system for performing a surgical procedure within the body of a subject, the robotic surgical system comprising:
    an elongate surgical instrument having a proximal end portion and a distal end portion;
    a robotic controller configured to control the motion of the distal end portion of the surgical instrument; and
    a mechanomyography feedback system in communication with the robotic controller, the mechanomyography feedback system including:
        an elongate sphincter contraction sensor including:
            an elongate device body configured to be inserted within a sphincter of the subject; and
            a force sensor in mechanical communication with the elongate device body and configured to provide a mechanomyography output signal in response to a contact force applied against the elongate device body by the sphincter;
        a processor configured to:
            receive the mechanomyography output signal;
            determine if the received mechanomyography output signal is indicative of an induced sphincter response that is attributable to the elongated surgical instrument; and
            provide a control signal to the robotic controller if an induced sphincter response is detected.

2. The robotic surgical system of claim 1, wherein the robotic controller is configured to limit the range of motion of the elongate surgical instrument in response to the received control signal.

3. The robotic surgical system of claim 1, wherein the robotic controller is configured to prevent motion of the distal end portion of the surgical instrument in response to the control signal.

4. The robotic surgical system of claim 1, wherein the control signal is indicative of a proximity between the distal end portion of the elongate surgical instrument and a nerve.

5. The robotic surgical system of claim 4, wherein the robotic controller is configured to vary the speed of the distal end of the elongate surgical instrument as a function of the indicated proximity.

6. The robotic surgical system of claim 1, wherein the processor of the mechanomyography feedback system is configured to determine if the received mechanomyography output signal is indicative of an induced sphincter response by:
    computing a time derivative of the contact force from the mechanomyography output signal;
    comparing the time derivative of the contact force to a threshold; and
    determining that the received mechanomyography output signal is indicative of an induced sphincter response if the time derivative of the contact force exceeds the threshold.

7. The robotic surgical system of claim 1, wherein the distal end portion of the surgical instrument includes a stimulator configured to provide an electrical stimulus.

8. The robotic surgical system of claim 7, wherein an induced sphincter response is an involuntary contraction of the sphincter against the elongate device body that is caused by the depolarization of a sacral nerve in response to the provided electrical stimulus.

9. The robotic surgical system of claim 1, wherein the elongate surgical instrument includes an end effector disposed at the distal end portion, the end effector being actuatable in at least one degree of freedom;
    wherein the robotic controller is configured to control the actuation of the end effector; and
    wherein the robotic controller is configured to prevent actuation of the end effector in response to the control signal.

10. The robotic surgical system of claim 1, wherein the elongate surgical instrument includes an end effector disposed at the distal end portion, the end effector being actuatable in at least one degree of freedom;
    wherein the robotic controller is configured to control the actuation of the end effector; and
    wherein the robotic controller is configured to actuate the end effector in response to the control signal.

11. The robotic surgical system of claim 1, further comprising a master station in communication with the robotic controller and configured to:
    receive an input from a user corresponding to an intended movement of the distal end portion of the surgical instrument; and
    provide a motion command to the robotic controller corresponding to the received input; and
    wherein the master station is configured to provide at least one of a visual alert and auditory alert if an induced muscle response is detected.

12. A method of nerve avoidance during robotically assisted surgery comprising:
    controlling the motion of a distal end portion of an elongate surgical instrument using a robotic controller the elongated surgical instrument being configured to provide a stimulus from the distal end portion;
    receiving a mechanomyography output signal from at least one elongate sphincter contraction sensor;
    determining if the received mechanomyography output signal is indicative of an induced sphincter response that is attributable to the stimulus provided by the elongated surgical instrument; and providing a control signal to the robotic controller if an induced sphincter response is detected.

13. The method of claim 12, further comprising electronically limiting the range of motion of the distal end portion of the elongate surgical instrument in response to the received control signal.

14. The method of claim 12, further comprising preventing, via the robotic controller, motion of the distal end portion of the surgical instrument in response to the control signal.

15. The method of claim 12, wherein the control signal is indicative of a proximity between the distal end portion of the elongate surgical instrument and a nerve.

16. The method of claim 15, further comprising varying the speed of the distal end portion of the elongate surgical instrument as a function of the indicated proximity.

17. The method of claim 12, wherein determining if the received mechanomyography signal is indicative of an induced sphincter response includes:
computing a time derivative of a contact force from the mechanomyography output signal;
comparing the time derivative of the contact force to a threshold; and
determining that the received mechanomyography output signal is indicative of an induced sphincter response if the time derivative of the contact force exceeds the threshold.

18. The method of claim 12, wherein the stimulus is an electrical stimulus; the method further comprising providing the electrical stimulus via a stimulator associated with the distal end portion of the elongate surgical instrument.

19. The method of claim 12, further comprising providing at least one of a visual alert and an auditory alert to a user if an induced muscle response is detected.

20. The method of claim 12, further comprising:
monitoring a contact force of at least one of an external sphincter of a bladder and an external sphincter of an anus of a subject against the elongate sphincter contraction sensor; and
generating the mechanomyography signal via the elongate sphincter contraction sensor, wherein the mechanomyography signal corresponds to the monitored contact force.

* * * * *